(12) United States Patent
Törmälä et al.

(10) Patent No.: US 6,248,108 B1
(45) Date of Patent: Jun. 19, 2001

(54) BIOABSORBABLE SURGICAL SCREW AND WASHER SYSTEM

(75) Inventors: Pertti Törmälä, Tampere (FI); James P. Tasto, San Diego, CA (US)

(73) Assignee: Bionx Implants Oy, Tampere (FI)

( * ) Notice: Subject to any disclaimer, the term of this patent is extended or adjusted under 35 U.S.C. 154(b) by 0 days.

(21) Appl. No.: 09/163,946

(22) Filed: Sep. 30, 1998

(51) Int. Cl.⁷ .................................................. A61B 17/58
(52) U.S. Cl. .............................................. 606/73; 411/533
(58) Field of Search .................... 606/61, 72, 73, 606/75, 77; 411/533

(56) References Cited

U.S. PATENT DOCUMENTS

| | | |
|---|---|---|
| 4,968,317 | 11/1990 | Törmälä et al. . |
| 4,988,351 * | 1/1991 | Paulos et al. ........................... 606/72 |
| 5,718,706 * | 2/1998 | Roger ..................................... 606/86 |
| 5,797,912 * | 8/1998 | Runciman et al. ..................... 606/73 |
| 5,810,816 * | 9/1998 | Roussouly et al. .................... 606/72 |
| B1 4,968,317 | 1/1999 | Törmälä et al. . |

* cited by examiner

Primary Examiner—Henry J. Recla
Assistant Examiner—Anthony S. King
(74) Attorney, Agent, or Firm—Kenyon & Kenyon

(57) ABSTRACT

An at least partially bioabsorbable surgical fastener or device formed in the shape of a screw and washer system and the methods for manufacturing and using the same. The surgical fastener is particularly but not solely intended to be used to attach rotator cuff tendons to bone.

9 Claims, 4 Drawing Sheets

BIOABSORBABLE SURGICAL SCREW AND WASHER SYSTEM

BACKGROUND OF THE INVENTION

The present invention relates to a surgical fastener or device (implant) formed in the shape of a screw and washer system and the method for manufacturing the same. The surgical implant of the present invention is particularly but not solely intended to be used in repair surgery for the tendons of the rotator cuff.

Tearing and degradation of the tendons of the rotator cuff muscles is a common and potentially painful and debilitative problem affecting thousands of people each year. The repair of the rotator cuff nearly always requires that the surgeon affix tendon to bone. Initially, surgical treatment of this condition required open surgery. To reduce the trauma of open surgery, arthroscopic surgical techniques have been developed to treat this condition. In both open and arthroscopic surgery, surgeons presently use sutures to affix torn tendons to the humeral head. Specifically, the surgeon will suture the tendon to the humeral head by drilling holes entirely through the bone and running the sutures through the holes (intraosseous or transosseous suturing). See e.g., Ellman, Gartsman, *Arthroscopic Shoulder Surgery and Related Procedures,* pp. 178–79, 189–97 (1993); and Iannotti, *The Rotator Cuff: Current Concepts and Complex Problems,* p. 18–19 (1998), the entire disclosures of each of which are incorporated herein by way of this reference.

The use of sutures can be problematic for several reasons. The surgeon must carefully drill holes entirely through the humeral head. Suturing the tendon to the bone through the drillhole is an intricate and exceedingly time consuming process, particularly when done arthroscopically. Sutures may easily break or tear out of the tissue that is being sutured, rendering the cuff repair a failure. Alternatively, sutures may stretch or otherwise allow portions of the repaired tendon to separate from the humeral head (causing diastasis), which results in poor tendon-to-bone healing. Sutures may also strangulate the tissue being sutured. Also, generally nonabsorbable sutures must be used because absorbable sutures degrade too quickly. These nonabsorbable sutures, however, represent a foreign body that can cause irritation or other post-operative problems in the shoulder joint.

In an attempt to prevent sutures from easily tearing out of a tendon, some surgeons have used small plates to help distribute the force of the sutures across a greater cross section of the tendon, as described, for instance, in EP 520,177, the entire disclosure of which is incorporated herein by way of this reference. Such plates, however, do not address the weakness of sutures generally or the difficulty and time-consuming nature of using sutures. Further, such plates can reduce vascularization of the tendon, resulting in tissue necrosis.

One alternative to intraosseous suturing is the use of a suture anchor in the humerus. The suture anchor is inserted into a hole in the humeral head and the tendon is thereby sutured to bone. However, little study has been done with suture anchors in the repair of rotator cuffs and there is a concern about the pull out strength of suture anchors. This is of particular concern where the humeral head has become osteoporotic. As a result, such suture anchors present a problem in rotator cuff repair surgery. If a suture anchor pulls out, not only is the cuff repair jeopardized, the anchor may cause further additional damage and/or discomfort within the shoulder joint. This procedure also has the aforementioned difficulties concerning the use of suturing in the tendon. Further, if the suture anchor is not made of a bioabsorbable material, then its continued presence in the humerus could lead to postoperative difficulties due to the patient's possible negative reaction to the foreign material of the anchor or migration of the anchor.

BRIEF SUMMARY OF THE INVENTION

Therefore, it is a goal of the present invention to provide a surgical fastener that is easy and quick to use, thereby reducing the length and difficulty of surgical procedures.

It is further a goal of the present invention to provide a surgical fastener that may, if desired, be used arthroscopically, thereby reducing operative trauma to the patient.

It is further a goal of the present invention to provide a surgical fastener strong enough and configured so as to effectively withstand the strong pull out forces involved with the fixation of rotator cuff tendons, thereby allowing proper healing of rotator cuff tears.

It is further a goal of the present invention to provide a fastener that is designed to firmly hold soft tissue to bone without damaging the soft tissue.

It is further a goal of the present invention to provide a surgical fastener that will biodegrade and is of minimum mass, thereby reducing the risk of post-operative complications due to the presence of the fastener in the patient.

It is further a goal of the present invention to provide a surgical fastener that has a low profile, thereby reducing irritation to the surrounding tissues.

It is further a goal of the present invention to provide a surgical fastener that may be self-tapping, thereby reducing the length and difficulty of surgical procedures.

It is further a goal of the present invention to provide a surgical fastener that exposes a broader surface area of the tendon to bone.

It is further a goal of the present invention to provide a method for manufacturing the surgical fastener having the aforementioned benefits. As can be seen from the following description, these and other goals are achieved through the present invention.

The surgical fastener of the present invention comprises a screw and a washer for attaching soft tissue to bone, such as attaching tendons of the rotator cuff to the humeral head. The screw is specially configured to have relatively tall threads for achieving strong purchase within the humeral head. The shank and head of the screw is relatively narrow, in order to minimize the mass of the screw and damage to the rotator cuff. The tip of the screw may be sharpened to form a trocar (pyramidal) or fluted cutting tip, for ease of insertion.

Surrounding the shaft of the screw of the present invention is a washer. The diameter of the annular opening of the washer through which the shaft of the screw passes is larger than the diameter of the shaft of the screw, yet smaller than the outer diameter of the threads and/or the head of the screw. Thus, the washer can freely slide up and down and rotate around the nonthreaded portion of the shaft, yet cannot be easily removed or otherwise separated from the screw without damaging the screw or the washer. The washer may further comprise relatively long protrusions or spikes on its lower surface. These spikes allow the washer to securely grip the soft tissue and hold it to the bone, yet are long enough so that the vascularity of the soft tissue is not compromised, thereby minimizing necrosis. The washer may also have a recess or indentation on its upper side for receiving the head of the screw so that the screw and washer have a low profile when inserted.

The screw and washer comprise a strong, durable biodegradable material. The material is preferably an oriented, fibrillated polymer/copolymer material, such as those described in U.S. Pat. No. 4,968,317, the entire disclosure of which is incorporated herein by way of this reference.

DETAILED DESCRIPTION OF THE INVENTION

Figure 1:
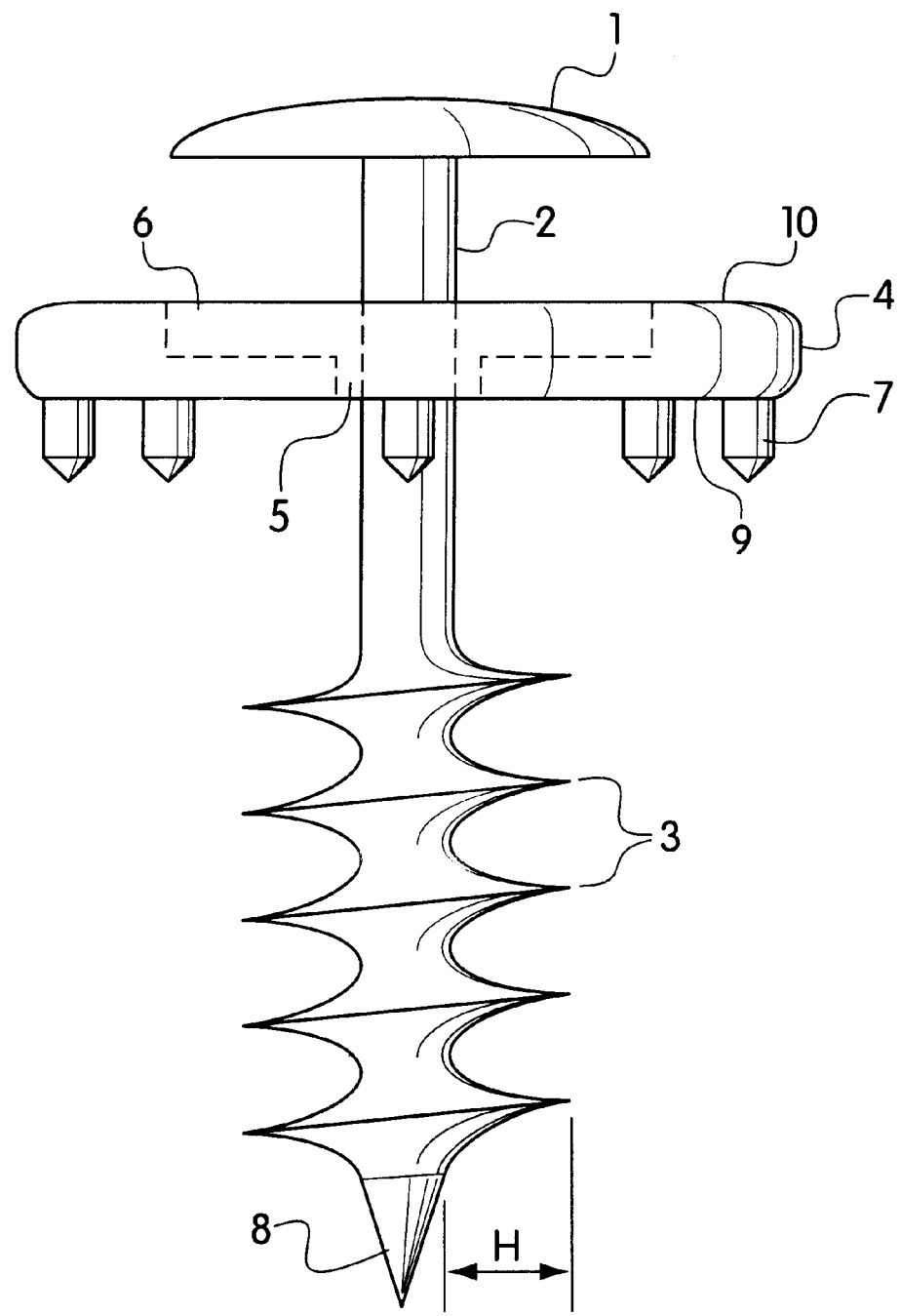
FIG. 1 depicts a side perspective view of an embodiment of the fastener of the present invention.

With reference to FIG. 1, it can be seen that the surgical fastener of the present invention comprises a screw and a washer combination. The screw has a head 1, a shank 2, and at least one thread 3. The shank 2 of the screw passes through the hole 5 in the washer 4.

One of the major difficulties faced in repairing injuries to the rotator cuff is fashioning a repair that will withstand the strong forces that are exerted on the tendons of the rotator cuff during and after the healing process. Previous screws have not been particularly successful in treating injuries to the rotator cuff because the tendons of the rotator cuff would easily pull the screws out of the humerus into which they were inserted. In order to withstand these forces, the screw of the present invention has been specially configured to have relatively tall threads 3. In a preferred embodiment of the present invention, at least a portion of the threads 3 have a height, "H", of at least 1.5 mm. These prominent threads provide the screw with greater stability once inserted into bone and allow the screw to attain higher pull out strengths in cancellous bone, such as the bone of the humeral head.

The threads 3 may take many different shapes. In a preferred embodiment of the present invention, the screw of the invention is self tapping. This simplifies the insertion procedure in softer bone and reduces the length of the repair operation.

Also in a preferred embodiment of the present invention, the tip 8 of the screw has a trocar, fluted, or pyramidal shape. This promotes the easy insertion of the screw into the bone. It also allows the screws to cut easily through the tendon that is being affixed to the bone, without causing unnecessary tearing or twisting of the tendon during the insertion of the screw.

Figure 2:
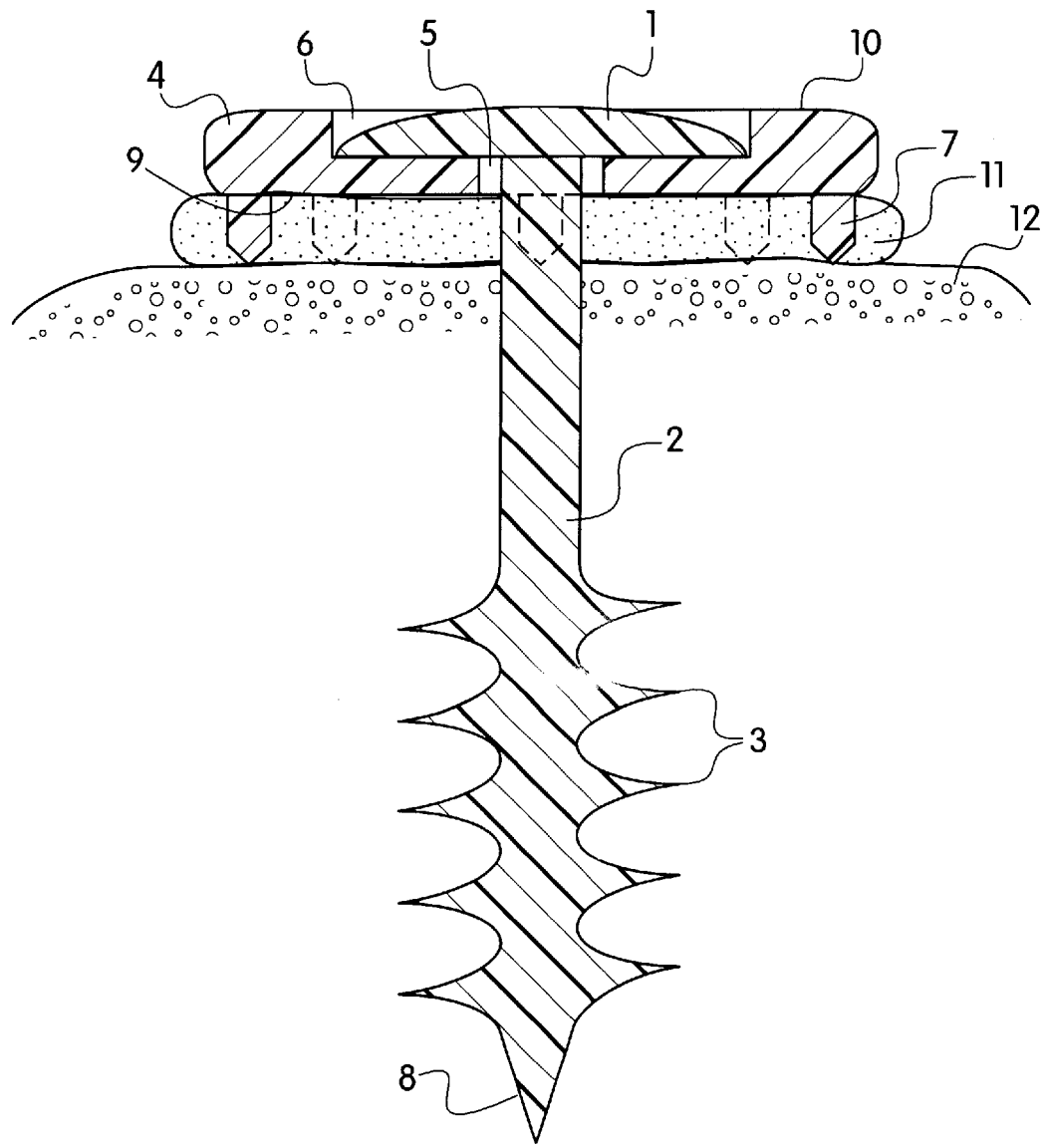
FIG. 2 depicts a partial cross sectional view of an embodiment of the fastener of the present invention being used to attach soft tissue to bone.
Figure 3:
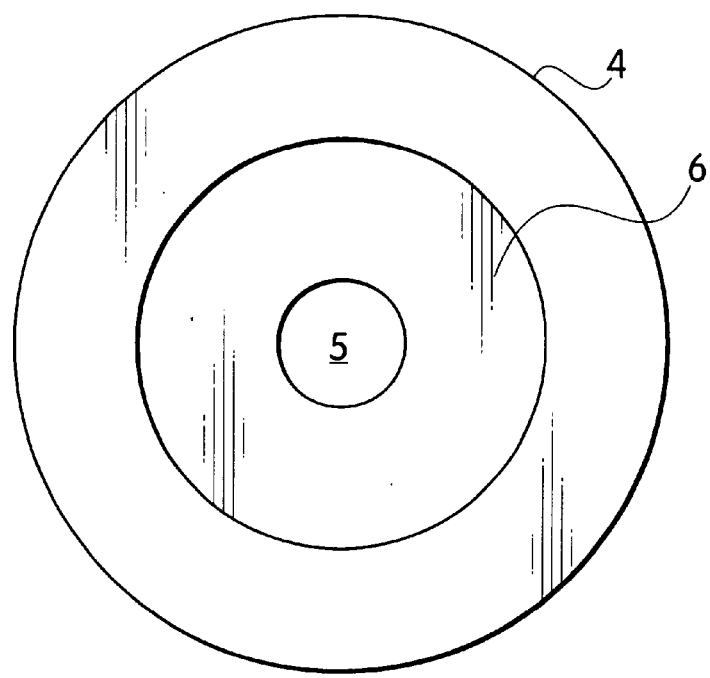
FIG. 3 depicts an embodiment of the upper side of the washer of the present invention.
Figure 4:
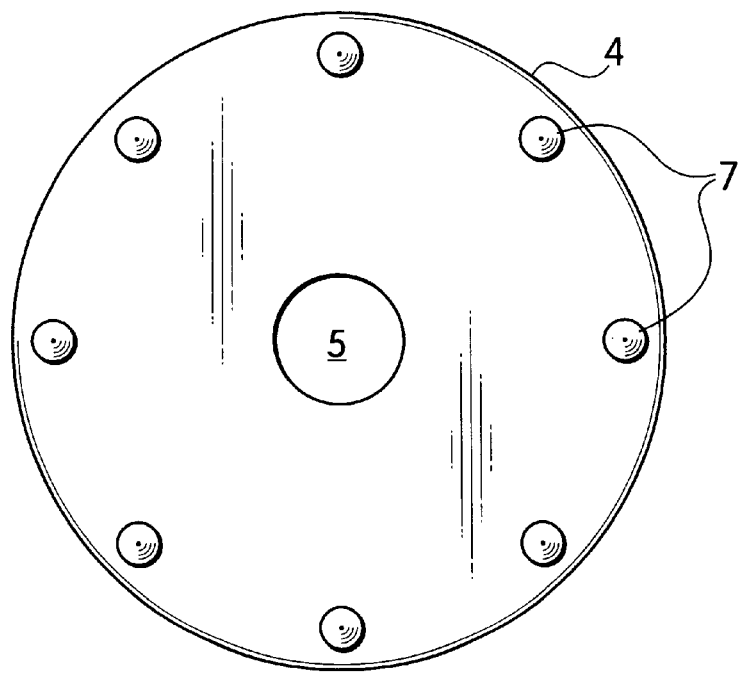
FIG. 4 depicts an embodiment of the lower side of the washer of the present invention.

The large surface area of the washer 4 effects greater fixation of the tendon to the bone distributed over a larger portion of the tendon. This reduces the risk that the tendon will tear from the screw, causing a failure of the repair. It also reduces the risk that the tendon will separate from the humeral head, causing instability in the shoulder joint. It also creates a broader surface area for tendon to bone healing and vascular ingrowth. In a preferred embodiment of the present invention, the lower surface 9 of the washer 4 has protrusions such as spikes 7, which grip the tendon, firmly affixing it to the bone and preventing unwanted slippage of the tendon during the healing process. As seen in FIG. 2, in yet another preferred embodiment of the present invention, the spikes 7 are long enough so that the flat lower surface 9 of the washer 4 is not pressed severely against the tendon 11 being repaired. In some instances, at least portions of the flat lower surface 9 of the washer will not contact the tendon 11. This allows good vascularization of the tendon 11 under repair and reduces the risk of tissue necrosis. Even though the lower surface 9 of the washer 4 does not compress the tendon 11 under repair severely enough to impair the vascularity of the tendon 11, the spikes 7 hold the tendon 11 firmly in place during the healing process. The spikes 7 are preferably from 0.6 to 3 mm in length. The spikes 7 may, but need not, contact the bone 12. The optimal size and shape of the spikes 7 will depend upon the specific repair to be done in an individual case and will, therefore, vary.

In another preferred embodiment of the present invention, the upper surface 10 of the washer 4 contains and indentation or recess 6. This recess 6 may be deep enough to receive the entire head 1 of the screw. Thus, when the screw is inserted into bone 12, the head 1 of the screw is located mainly or entirely within the recess 6 of the washer 4. This reduces the profile of the device of the present invention when inserted, thereby reducing the risk of irritation or damage to the surrounding tissues.

The cross section of the washer 4 may have various shapes, including those with rounded edges, in order to reduce the profile of the inserted device and further reduce the risk of irritation or damage to the surrounding tissues. Similarly, the cross section of the head 1, may have different shapes and sizes, depending upon the particular application for which the fastener is being used.

In a preferred embodiment of the present invention, the device is made of an at least partially absorbable material, such as polylactides, polyglycolides, and copolymers thereof. It should be understood, however, that the present invention may be made from a variety of bioabsorbable materials, a partial list of which is included in U.S. Pat. No. 4,968,317. Additionally, in another preferred embodiment of the present invention, the washer 4 is made of a material that bioabsorbs faster than the material from which the screw is constructed. This reduces the risk that the screw will degrade first, allowing the washer to separate from the tendon or bone and cause irritation or damage to surrounding tissues. Preferably, the washer 4 will be constructed of a material that will retain much of its strength for 4–6 months. This allows enough time for the tendon to heal properly before the washer begins to substantially degrade. The use of bioabsorbable materials reduces the risks related to the use of permanent implants, including irritation, rejection, and the possibility of a second procedure to remove the implant. Further, bioabsorbable implants cause less interference with postoperative MRIs and X-rays, than do metallic implants.

In another preferred embodiment of the present invention, the device is constructed of bioabsorbable material that has been oriented and fibrillated. Procedures for orienting and fibrillating polymers to increase their strength are known in the art and are described, for instance, in U.S. Pat. No. 4,968,317. In another preferred embodiment, the washer 4 is made from a material that has been biaxially oriented. Such orientation increases the strength of the device, allowing for more secure fixation of tendon to bone.

In another embodiment of the present invention, the bioabsorbable material from which the device is constructed may also contain other elements, such as medication, growth hormones, or other biomaterials that promote growth and healing of tissue.

The screw and washer combination of the present invention greatly reduces the amount of time needed to effect a repair of the rotator cuff. Further, it is far easier to use than previously developed suturing techniques. This is particularly true when the present invention is used arthroscopically. Complicated and intricate knot tying is replaced with simply inserting the screw through the tendon 11 and into the bone 12. Depending upon the strength and hardness of the bone 12, a hole may have to be drilled into the bone 12 prior to inserting the screw, or the screw may be self tapping if the bone 12 is relatively soft. As the screw is inserted, the washer 4 holds the tendon 11 against the bone 12. While the screw is being screwed into the bone 12, the washer 4 may rotate around the shank 2 of the screw. Thus, once the washer 4 contacts the tendon 11, it stays in place relative to the tendon 11, while the screw continues to be screwed into the bone 12. This ensures that the tendon 11 does not get twisted or unnecessarily damaged during the insertion of the screw. Although the present invention is particularly useful for arthroscopic surgical procedures, it may also be used in open procedures as well.

Due to the relatively tall threads 3 on the screw, and the relatively small hole 5 in the washer 4, the washer 4 cannot be removed from the screw without damaging either the screw or the washer 4. This ensures that the washer 4 will not be inadvertently separated from the screw before or during the insertion procedure. This also simplifies the operation because the surgeon or his assistants do not have to place the washer on the screw before the operation, possibly increasing the risk of contamination of the sterile implant.

Figure 5:
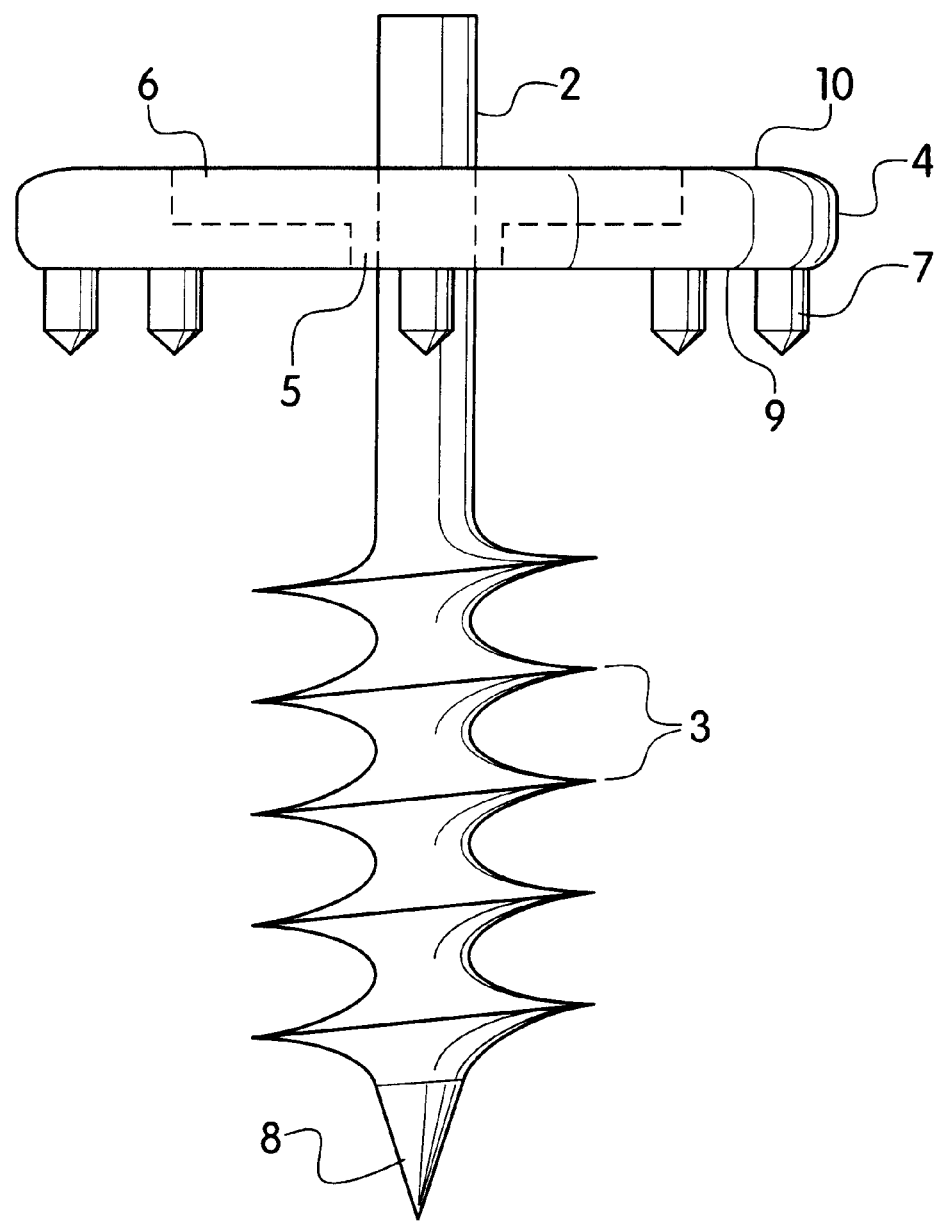
FIG. 5 depicts an embodiment of the fastener of the present invention during the manufacturing process, before the head of the screw has been formed.

In order to achieve this result, however, it is preferable that the screw and the washer 4 be manufactured together. Thus, the washer 4 of the present invention preferably is placed onto the shank 2 of the screw before the head 1 of the screw is formed. This is illustrated in FIG. 5. The shank 2 and threads 3 of the screw are formed through techniques known in the art. The head 1, however, is missing from the screw. At this point, the fully formed washer 4 is placed over the shank 2 of the screw. The washer 4 is also formed using techniques known in the art. These could include techniques such as extrusion, injection molding, and machining. Once the washer 4 is placed around the shank 4 of the screw, the head 1 of the screw is formed from the material at the top of the shank 2. This forming step could be achieved, for instance by machining the top of the shank 2. Once the head 1 of the screw is formed, the washer 4 cannot be easily removed from the screw without damaging either the screw or the washer 4.

After the description above of the present invention and certain specific embodiments thereof, it will be readily apparent to those skilled in the art that many variations and modifications may be made to the present invention without departing from the spirit and scope thereof. The following example is intended to be illustrative only, and in no way limits the scope of the invention.

EXAMPLE 1

Pull out strength tests were performed on a fastener of the present invention. The tests were performed on the tibia of a cadaverous pig. The meniscus was scraped away from the cartilage surface and a 3.2 mm diameter hole was drilled through this surface. Subsequently, a shallower 9 mm diameter hole was drilled though the compact surface bone layer. The deep 3.2 mm hole was tapped. A screw and washer, the screw having threads with an outer diameter of about 6.8 mm and an inner diameter of about 3.7 mm, and both being constructed from poly-L-lactide (PLLA), were inserted into the bone with a driver tool having a square tip corresponding to the slot on the head of the screw. The head of the screw was left just above the cartilage surface. A suture was attached to the shank of the screw and the screw was pulled out of the bone. The force required to remove the screw was measured. Over a series of ten trials, the screw withstood a pull out force of 150 to 260 N.

We claim:

1. A surgical fastener comprising:
an at least partially bioabsorbable screw made from a bioabsorbable material that is oriented or fibrillated comprising: a distal end, a proximal end having a head having a first diameter and a height, a shank having a second diameter and connected to said head, and at least one thread having an outer diameter and an inner diameter, wherein at least a portion of said thread has a height of at least 1.5 mm;
an at least partially bioabsorbable annular washer having upper and lower sides and a opening therethrough, said upper side facing said head of said screw,
said shank of said screw passing through said opening in said washer, and
said opening having a third diameter that is: larger than the second diameter of said shank; smaller than the first diameter of said head; and smaller than the outer diameter of said thread; wherein the washer degrades faster in vivo than the screw.

2. The fastener of claim 1 wherein the at least partially bioabsorbable material is oriented or fibrillated.

3. The fastener of claim 1 wherein the washer comprises an at least partially bioabsorbable material that is biaxially oriented or fibrillated.

4. The fastener of claim 1 wherein the washer further comprises a plurality of protrusions protruding from the lower side of said washer.

5. The fastener of claim 4 wherein at least one of the protrusions is at least 0.6 mm in height.

6. The fastener of claim 5 wherein the upper side of said washer contains an indentation configured to removably receive at least a portion of said head of said screw.

7. The fastener of claim 6 wherein the indentation has a depth that is greater or equal to the height of the head of the screw.

8. The fastener of claim 1 wherein the pull out force of the fastener is at least 150 N.

9. The fastener of claim 1 wherein the distal end of the screw has a trocar tip.

* * * * *